United States Patent [19]

Bradley et al.

[11] Patent Number: 5,626,128
[45] Date of Patent: May 6, 1997

[54] ENDOTRACHEAL TUBE FIXATION DEVICE AND METHOD OF USING THE SAME

[75] Inventors: J. Warren Bradley; Richard L. Wilson, both of Mount Pleasant, S.C.

[73] Assignee: University of South Carolina, S.C.

[21] Appl. No.: 520,934

[22] Filed: Aug. 31, 1995

[51] Int. Cl.$^6$ ................................................ A61M 16/00
[52] U.S. Cl. ........................... 128/200.26; 128/207.14; 128/207.15; 128/206.29
[58] Field of Search .................. 128/200.26, 207.14, 128/207.15, 206.25, 206.29

[56] References Cited

U.S. PATENT DOCUMENTS

| 3,139,088 | 6/1964 | Galleher | 128/206.29 |
|---|---|---|---|
| 3,993,081 | 11/1976 | Cussell | 128/207.14 |
| 4,192,785 | 3/1980 | Chen et al. | 128/206.25 |
| 4,356,821 | 11/1982 | Rind | 128/207.14 |
| 4,360,025 | 11/1982 | Edwards | 604/180 |
| 4,516,293 | 5/1985 | Beran | 24/16 PB |
| 4,683,882 | 8/1987 | Laird | 128/207.17 |
| 4,932,943 | 6/1990 | Nowak | 604/180 |
| 4,986,815 | 1/1991 | Schneider | 604/180 |
| 5,043,576 | 8/1991 | Broadhurst et al. | 250/293 |
| 5,048,519 | 9/1991 | Kasama et al. | 128/206.29 |
| 5,069,206 | 12/1991 | Crosbie | 128/207.17 |
| 5,263,478 | 11/1993 | Davis | 128/207.14 |

FOREIGN PATENT DOCUMENTS 2643269A  8/1990  France.

OTHER PUBLICATIONS

Shahrbanoo, et al., "*Use of a palatal stabilizing device in prevention of palatal grooves in premature infants*" Critical Care Medicine vol. 18 No. 7,1279–1281 (Jul., 1990).

*Primary Examiner*—Aaron J. Lewis
*Attorney, Agent, or Firm*—Needle & Rosenberg, PC

[57] ABSTRACT

A medical device for internally maintaining by means of an oral adhesive composition an endotracheal tube in proper position in a patient's mouth and protecting the patient from endotracheal intubation associated injury, as well as subsequently permitting adjustment of the endotracheal tube relative to the device. The device has a heat-sensitive moldable polymer on its superior surface for adaptation to individual patient's oral cavities. The invention also prevents endotracheal tube occlusion from patient jaw closure, and is particularly well-adapted for patients suffering from facial burns, dermatitis, or cleft palate syndrome. A method of using the device is also disclosed.

19 Claims, 1 Drawing Sheet

ENDOTRACHEAL TUBE FIXATION DEVICE AND METHOD OF USING THE SAME

BACKGROUND OF THE INVENTION

1. Field of the Invention

This invention relates to the field of endotracheal tubes and, more particularly, to a device for maintaining the tube in the proper position in the patient's upper respiratory tract.

2. Description of the Prior Art

Patients of all ages may require endotracheal intubation as a life sustaining measure. A frequent complication of endotracheal intubation and airway maintenance is physical trauma caused to the lips, oral membranes, dentitia, gums, larynx, trachea and bronchi. In addition, malpositioned or dislodged endotracheal tubes may result in inadequate ventilation and oxygenation, which can lead to permanent neurological damage and death. Hyperventilation resulting from malpositioned tubes may lead to disturbances of the normal balance between ventilation and perfusion, and life threatening air leak syndromes, such as pneumomediastinum, pneumothorax, and pneumopericardium.

Even with initially properly positioned endotracheal tubes secured by currently available means, intratracheal tube movement and sliding resulting from the vibrations associated with mechanical ventilators and normal patient movements can cause permanent damage to the patient's larynx or airways, such as laryngeal paralysis. In some patients, endotracheal associated damage to bronchial mucosa can result in airway scarring (granulation tissue), hyperplasia (bronchial malacia), resultant airway stenosis, and subsequent increases in both mortality and morbidity.

Conventional methods of endotracheal tube fixation involve placing adhesives, such as tape, or fixation straps externally around the patient's face, neck, head, or lips. For example, see U.S. Pat. Nos. 5,263,478; 5,069,206; 4,683,882; and 3,993,081. Patients suffering from facial burns, dermatitis or cleft palate syndrome are currently dependent upon these externally secured devices, which are very undesirable, painful and impractical. In infants, externally secured endotracheal tube fixation devices are also unsatisfactory because circumferential fasteners around the infant's neck may restrict cerebral blood flow, and application of adhesives directly to the skin can result in dermal degradation.

One available device designed for neonates may be found in U.S. Pat. No. 5,195,513 entitled "Infant Palate Protective Prosthesis," which provides for securing the device externally by conventional methods of taping or strapping. Although the device theoretically provides protection from palatal grooving caused by endotracheal tube movement, it still relies on conventional fixation methods to secure both itself and the endotracheal tube. The use of such a device, therefore, does not address the problems associated with conventional methods, such as dermal damage, decreased cerebral blood flow, or the hazards associated with malpositioned or dislodged endotracheal tubes.

Another common form of prior art device suitable for pediatric and adult populations, but not applicable in infants and neonates may be characterized as a bite block. See, for example, U.S. Pat. No. 5,069,206. In devices of this type, an element of the device is positioned circumferentially, inferior and superior to, or otherwise surrounding the endotracheal tube, and positioned between the patient's upper and lower dentitia. The device is then secured conventionally to the head and face with tape, external adhesive elements, or strapping. The endotracheal tube is affixed to the device itself with a system of elastic straps or locking clips. Although the device theoretically prevents endotracheal tube occlusion by patient biting, and provides a relatively secure endotracheal tube position, it does not avoid the hazards associated with traditional external fixation methods.

In other available devices, the endotracheal tube is affixed to the device itself by either conventional adhesive methods or with any of a great variety of locking devices. See, for example, U.S. Pat. Nos. 4,360,025; and 4,516,293. However, these fixation means are not satisfactory for effectively preventing endotracheal tube slippage.

Other available devices, such as dental protectors or palatal stabilizers, generally provide a mouthpiece adhered in the patient's oral cavity by an adhesive or a gelatinous insert. Such devices are designed to cover and adhere to the patient's teeth, thereby providing a physical barrier to prevent intubation associated trauma or longer term palatal grooving. These devices, however, do not provide a means for affixing an endotracheal tube in position, but rather are presented as mere protective prosthetics.

Thus, all the prior art devices may be characterized as either external fixation systems or protective prosthetics and are of limited effectiveness. Available external fixation devices are not useful in securing the precise intratracheal position of the endotracheal tube distal tip, nor are they useful, in completely preventing movement or sliding of the tube within the trachea. Further, the prior art devices are associated with the limitations and hazards of conventional external fixation means. None of the devices is suitable for use in all patient populations, and they do not provide adequate protection for the dentitia, lips, gums or upper respiratory tract during insertion of the endotracheal tube.

It should, therefore, be apparent that an improved, simple, inexpensive, protective, internally secured, endotracheal tube insertion and fixation device which is suitable for patients of all ages, is needed to prevent complications and hazards associated with the use of all the prior art devices.

OBJECTS OF THE INVENTION

It is an object of the present invention to provide an endotracheal tube fixation device which can be maintained in a patient's mouth without conventional external adhesive means.

It is a further object of the invention to provide an endotracheal tube fixation device having a means for affixing the endotracheal tube for adjustable positioning without slippage.

It is a further object of the invention to provide an endotracheal tube fixation device having a polymer which is moldable to conform to the particularities of an individual patient's mouth.

It is a further object of the invention to provide an endotracheal fixation tube fixation device which prevents biting occlusion of the endotracheal tube during use.

SUMMARY OF THE INVENTION

The invention provides a medical device for internally maintaining by means of an oral adhesive composition an endotracheal tube in proper position in a patient's mouth and protecting the patient from endotracheal intubation associated injury. The invention provides a device which secures the endotracheal tube in the desired position, and subsequently permits adjustment of the endotracheal tube relative to device. The medical device has a heat-sensitive moldable polymer on its superior surface for adaptation to individual patient's oral cavities. The invention also provides a medical device for preventing endotracheal tube occlusion from patient jaw closure. The invention is particularly well-adapted for patients suffering from facial burns, dermatitis, or cleft palate syndrome.

DETAILED DESCRIPTION OF THE ILLUSTRATIVE EMBODIMENT

Figure 1:
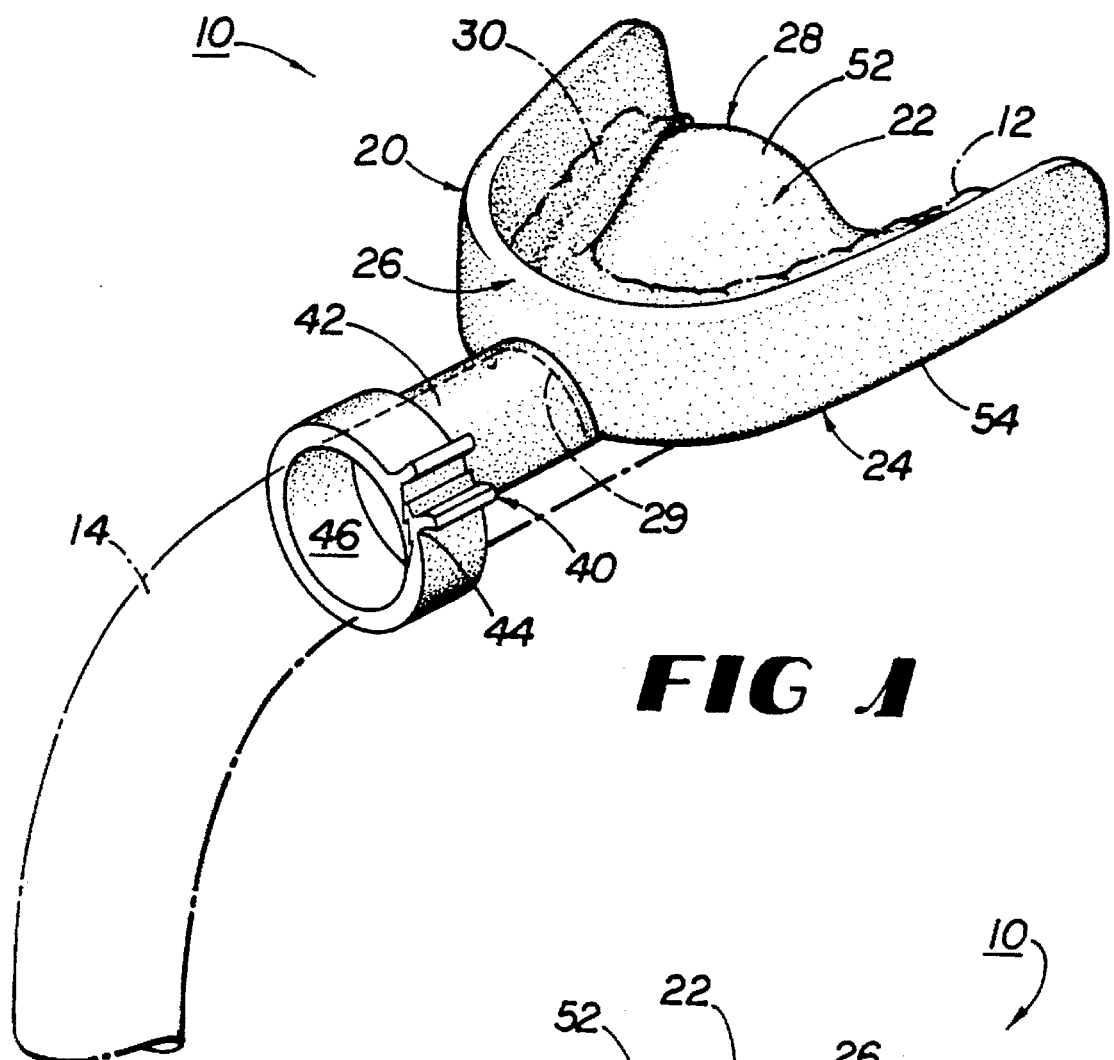
FIG. 1 is a perspective view of the endotracheal tube fixation device of the present invention with the endotracheal tube shown in phantom lines.
Figure 2:
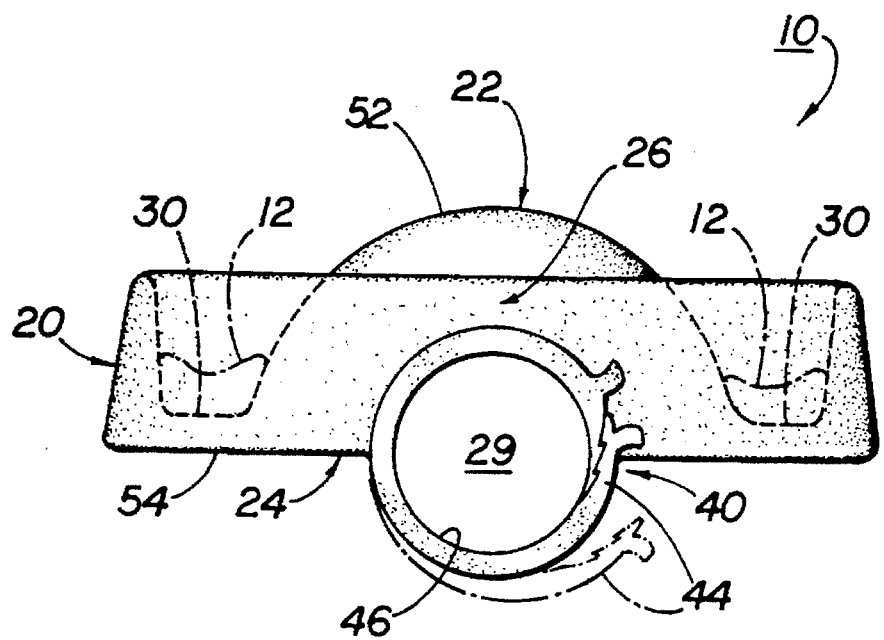
FIG. 2 is a front end elevational view of the endotracheal tube fixation device of the present invention with the endotracheal tube affixing means shown alternatively in the open position in phantom lines.

As seen in FIGS. 1 and 2, the invention provides a medical device 10 for maintaining by means of an oral adhesive composition 12 an endotracheal tube 14 in proper position in a patient's mouth. The device 10 protects the patient from endotracheal intubation associated injury, including injury to the facial or cranial skin, lips, oral membranes, gums, forming and/or established dentitia, larynx, trachea and upper airways resulting from endotracheal tube 14 positioning and airway maintenance.

The device 10 has a body member 20 with a superior (upper) surface 22, an inferior (lower) surface 24, an anterior (front) aspect 26 and a posterior (rear) aspect 28. The body member 20 defines a passage 29 for receiving an endotracheal tube 14 through the anterior aspect 26 thereof. The superior surface 22 of the body member 20 is complimentarily (arcuately) shaped for positioning against the patient's superior and anterior oral cavity.

The body member 10 is generally semicircular in shape, and is composed of an injection molded, biologically compatible, semi-rigid, minimally deformable, plastic polymer. The device 10 is intended to be available in variety of standard sizes categorized by scaled age and weight to the normal morphologic characteristics of the gums and/or dentitia, and upper buccal cavity. These standards may be obtained from molds of similarly sized healthy individuals.

A channel 30 is integrally formed on the superior surface 22 of the body member 20 in a position corresponding to the patient's upper teeth or gums. The channel 30 is adapted for receiving an oral adhesive composition 12 for temporarily maintaining the body member 20 in the patient's mouth. The oral adhesive composition 12 can be applied, for example, as a liquid, viscous cream or powder. The adhesive ingredient may be, for example, a natural or synthetic gum (e.g., cellulose gum), vinyl methyl ether maleate, or another oral adhesive material known to those skilled in the art. The active adhesive ingredient can be suspended in an inert base depending upon the intended form of administration, such as petrolatum for viscous creams. Commercial oral adhesive compositions are readily available, including, for example, FIXODENT (Proctor & Gamble, Cincinnati, Ohio), or POLI-GRIP (Dentco, Jersey City, N.J.).

Thus, the invention provides a device for maintaining the endotracheal tube 14 in a patient's mouth without conventional external fixation means, such as skin adhesives, tapes or straps. This is particularly advantageous to patients suffering from facial burns or dermatological complications. Additionally, infant patients with cleft palate syndrome or underdeveloped cranial blood vessels will greatly benefit from this invention.

The adhesive composition 12 may further comprise a bacteriostatic, anti-bacterial, fungistatic, or fungicidal agent, or a combination thereof. The effect of adding such agents, which are well-known to those skilled in the art, to the adhesive composition 12 will allow the device 10 to be maintained in the patient's mouth for an extended period of time. For example, salts and preservatives may be added. Furthermore, the dental adhesive may comprise various colorings and flavorings, (e.g., menthol), to appeal to the particular class of individuals intended to use the invention.

A means 40 is also provided for affixing the endotracheal tube 14 to the body member 20 of the medical device 10. The endotracheal tube fixation means 40 has a forward portion 42 extending from the anterior aspect 22 of the body member 20 about the endotracheal tube passage 29 and terminating in a forward end clamping means 44. This endotracheal tube affixing means 40 selectively maintains the endotracheal tube 14 in proper position, allowing for periodic adjustments.

In a preferred embodiment, the clamping means 44 is a flexible element having opposed ends and an adjustable rachet and pawl thereon for circumferentially gripping the exterior surface of the endotracheal tube 14, and thus securing its movement. As shown by the phantom line in FIG. 2, the rachet and pawl may be disengaged into the open position for positioning the tube 14 relative to the body member 20.

The clamping means 44 also has an interior surface 46 and means on the interior surface 46 for preventing slipping movement of said endotracheal tube 14. The interior surface 46 of the tube clamping means 44 may be adapted with an adhesive, or be stippled or grooved, or otherwise arranged with raised projections (not shown) for securely engaging and thus gripping, the endotracheal tube 14 to prevent slippage.

In one preferred embodiment, the body member 20 further comprises a first polymer 52 defining the superior surface 22 and a second polymer 54 defining the inferior surface 24 thereof. Preferably, the first polymer 52 defining the superior surface 22 is more resiliently deformable than the second polymer 54 defining the inferior surface 24. This feature permits better conformation to the oral contours of the individual patient. The second polymer 54 defining the inferior surface 24 may be somewhat more resiliently stiff to resist the forces of the lower jaw and dentitia against the body member 20, and to prevent endotracheal tube 14 occlusion due to biting. When constructing the device 10, the first and second polymers 52, 54 may be fused directly together, or each may be disposed upon a base layer.

More preferably, the first polymer 52 defining the superior surface 22 is moldable at a lower temperature than the second polymer 54. Therefore, the device 10 may be dipped in hot water for several minutes, for example, and inserted into the patient's mouth for molding the first polymer 52 defining the superior surface 22 to the exact contours of the individual. Preferably, the second polymer 54 defining the inferior surface 24 remains more resiliently stiff, and not moldable during this process. Such polymers can be differing compositions of methylmethaerglate, for example.

In another preferred embodiment, the posterior aspect 28 of the body member 20 is thicker than the anterior aspect 26 at the position corresponding to the patient's teeth or gums. Thus, a proportionally sized wedge-shaped extension may be formed by the posterior aspect 28 of the device 10 to prevent complete jaw closure and endotracheal tube 14 occlusions.

The invention further provides a method of maintaining, by means of an oral adhesive composition 12, an endotracheal tube 14 in proper position in a patient's mouth and protecting the patient from endotracheal intubation associated injury using the above-described device. The method comprises the steps of applying an effective mount of the adhesive composition along the channel; inserting the body member into the patient's mouth against the superior and anterior oral cavity; positioning the endotracheal tube in proper position in the patient's mouth; and affixing the endotracheal tube to the body member. The method can include the additional first step of molding the first polymer of the device to conform to the contours of the patient's superior and anterior oral cavity.

As used herein, "a" means one or more than one depending upon the context within which it is used. The examples described herein are intended to illustrate, but not limit the invention. It will be appreciated by one skilled in the art that a variety of alternate embodiments are contemplated by the scope and spirit of disclosure of the present invention.

What is claimed is:

1. An medical device for maintaining by means of an oral adhesive composition an endotracheal tube having an exterior surface in proper position in a patient's mouth and protecting a patient from endotracheal intubation associated injury, comprising:
   a. a body member having a superior surface, an inferior surface, an anterior aspect and a posterior aspect, said body member defining a passage for receiving an endotracheal tube through the anterior aspect thereof, and said superior surface being complimentarily shaped to a patient's superior and anterior oral cavity for positioning thereagainst;
   b. a channel integrally formed on said superior surface of said body member in registry with a patient's upper teeth or gums, adapted for receiving the adhesive composition for temporarily maintaining said body member in a patient's mouth; and,
   c. means for affixing an endotracheal tube to the body member, comprising a forward portion extending from said anterior aspect of said body member about said endotracheal tube passage and terminating in a forward end and a clamping means on the forward end for selectively maintaining an endotracheal tube in proper position.

2. The device of claim 1, wherein said clamping means is a flexible element having opposed ends and a rachet and a pawl on respective ends which cooperate to lock the flexible element about the exterior surface of an endotracheal tube.

3. The device of claim 1, wherein the flexible element has an interior surface with means thereon for preventing slipping movement of an endotracheal tube.

4. The device of claim 1, wherein said adhesive composition comprises a bacteriostatic, anti-bacterial, fungistatic, or fungicidal agent.

5. The device of claim 1, wherein said oral adhesive composition comprises a dental adhesive.

6. The device of claim 1, wherein said body member further comprises a first polymer defining said superior surface and a second polymer defining said inferior surface thereof.

7. The device of claim 6, wherein said first polymer is more resiliently deformable than said second polymer.

8. The device of claim 7, wherein said first polymer is moldable at a lower temperature than said second polymer.

9. The device of claim 1, wherein said posterior aspect is thicker than said anterior aspect at the position which is in registry with a patient's teeth or gums.

10. A method of maintaining by means of an adhesive composition an endotracheal tube on a medical device in proper position in a patient's mouth and protecting the patient from endotracheal intubation associated injury, the method comprising:

providing a body member having a superior surface, an inferior surface, an anterior aspect and a posterior aspect, said body member defining a passage for receiving an endotracheal tube through the anterior aspect thereof, and said superior surface being complimentarily shaped to the patient's superior and anterior oral cavity for positioning thereagainst;

providing a channel integrally formed on said superior surface of said body member in registry with the patient's upper teeth or gums, adapted for receiving the adhesive composition for temporarily maintaining said body member in the patient's mouth; and, providing means for affixing an endotracheal tube to the body member, comprising a forward portion extending from said anterior aspect of said body member about said endotracheal tube passage and terminating in a forward end and a clamping means on the forward end for selectively maintaining an endotracheal tube in proper position;
   a. applying an effective amount of the adhesive composition along the channel;
   b. inserting the body member into the patient's mouth against the superior and anterior oral cavity;
   c. positioning an endotracheal tube in proper position in the patient's mouth; and,
   d. affixing an endotracheal tube to the body member.

11. The method of claim 10, further comprising providing said clamping means as a flexible element having opposed ends and a rachet and a pawl on respective ends which cooperate to lock the flexible element about the exterior surface of an endotracheal tube.

12. The method of claim 10, further comprising: providing the flexible element with an interior surface with means thereon for preventing slipping movement of an endotracheal tube.

13. The method of claim 10, further comprising: providing said adhesive composition as a bacteriostatic, anti-bacterial, fungistatic, or fungicidal agent.

14. The method of claim 10, further comprising said oral adhesive composition as a dental adhesive.

15. The method of claim 10, further comprising: providing said body member as a first polymer defining said superior surface and a second polymer defining said inferior surface thereof.

16. The method of claim 15, further comprising: making said first polymer more resiliently deformable than said second polymer.

17. The method of claim 16, further comprising: molding said first polymer at a lower temperature than said second polymer.

18. The method of claim 17, further comprising the additional first step of molding the first polymer of the medical device to conform to the contours of the patient's superior and anterior oral cavity.

19. The method of claim 10, further comprising: making said posterior aspect thicker than said anterior aspect at the position which is in registry with the patient's teeth or gums.

* * * * *

UNITED STATES PATENT AND TRADEMARK OFFICE
CERTIFICATE OF CORRECTION

PATENT NO. : 5626128
DATED : May 6, 1997
INVENTOR(S) : J. Warren Bradley, Richard L. Wilson It is certified that error appears in the above-identified patent and that said Letters Patent is hereby corrected as shown below:

On the title page, item [73], should read
--Assignee: Medical University of South Carolina--

Signed and Sealed this

First Day of September, 1998

Attest:

BRUCE LEHMAN

*Attesting Officer*     *Commissioner of Patents and Trademarks*